United States Patent
Pal et al.

(10) Patent No.: US 9,074,986 B2
(45) Date of Patent: Jul. 7, 2015

(54) SYSTEM AND METHOD FOR REDUCING HIGH DENSITY ARTIFACTS IN COMPUTED TOMOGRAPHY IMAGING

(71) Applicant: General Electric Company, Schenectady, NY (US)

(72) Inventors: Debashish Pal, Waukesha, WI (US); Jiang Hsieh, Brookfield, WI (US); Paavana Sainath, Oconomowoc, WI (US); Girijesh Yadava, Waukesha, WI (US); Brian Edward Nett, Madison, WI (US)

(73) Assignee: General Electric Company, Schenectady, NY (US)

( * ) Notice: Subject to any disclaimer, the term of this patent is extended or adjusted under 35 U.S.C. 154(b) by 223 days.

(21) Appl. No.: 13/875,369

(22) Filed: May 2, 2013

(65) Prior Publication Data

US 2014/0328450 A1 Nov. 6, 2014

(51) Int. Cl.
| | |
|---|---|
| *G01N 23/04* | (2006.01) |
| *G01V 5/00* | (2006.01) |
| *A61B 6/03* | (2006.01) |
| *A61B 6/00* | (2006.01) |

(52) U.S. Cl.
CPC .............. *G01N 23/046* (2013.01); *G01V 5/005* (2013.01); *A61B 6/032* (2013.01); *A61B 6/482* (2013.01); *A61B 6/488* (2013.01); *A61B 6/5258* (2013.01); *A61B 6/545* (2013.01)

(58) Field of Classification Search
CPC ............................. A61B 6/032; A61B 6/5258
USPC ............................................................ 378/7
See application file for complete search history.

(56) References Cited

U.S. PATENT DOCUMENTS

| | | | |
|---|---|---|---|
| 2009/0283682 A1 * | 11/2009 | Star-Lack et al. .......... | 250/363.1 |
| 2011/0081071 A1 | 4/2011 | Benson et al. | |

OTHER PUBLICATIONS

"CT metal artifact reduction method correcting for beam hardening and missing projections"; Authors Joost M. Verburg and Joao Seco; Published Apr. 18, 2012 in Physics in Medicine and Biology.
"Reduction of computed tomography metal artifacts due to the Fletcher-Suit applicator in gynecology patients receiving intracavitary brachytherapy"; Authors John Roeske, Christina Lund, Charles Pelizzari, Xiaochuan Pan, Arno Mundt; Aug. 2003.
"Minimizing Clip Artifacts in Multi CT Angiography of Clipped Patients"; Authors van der Schaaf, van Leeuwen, Vlassenbroek, Velthuis; Published Jan. 2006 issue of AJNR.

* cited by examiner

*Primary Examiner* — Hoon Song
(74) *Attorney, Agent, or Firm* — Lucas Divine; General Electric Company (57) ABSTRACT

An imaging system includes a rotatable gantry for receiving an object to be scanned, a generator configured to energize an x-ray source to generate x-rays, a detector positioned to receive the x-rays that pass through the object, and a computer. The computer is programmed to obtain knowledge of a metal within the object, scan the object using system scanning parameters, reconstruct an image of the object using a reconstruction algorithm, and automatically select at least one of the system scanning parameters and the reconstruction algorithm based on the obtained knowledge.

15 Claims, 4 Drawing Sheets

SYSTEM AND METHOD FOR REDUCING HIGH DENSITY ARTIFACTS IN COMPUTED TOMOGRAPHY IMAGING

BACKGROUND

This disclosure relates generally to diagnostic imaging and, more particularly, to an apparatus and method of reducing artifacts due to high-density objects in computed tomography (CT).

Typically, in computed tomography (CT) imaging systems, an x-ray source emits a fan or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are transmitted to the data processing system for image reconstruction. Imaging data may be obtained using x-rays that are generated at a single polychromatic energy. However, some systems may obtain multi-energy images that provide additional information for generating images.

Objects with high x-ray absorption properties (e.g., metal) can cause artifacts in reconstructed CT images, often resulting in images having low or non-diagnostic image quality. For example, metal implants such as amalgam dental fillings, joint replacements (i.e., plates and/or pins used in hips, knees, shoulders, etc.), surgical clips, biopsy needles, or other hardware may generate streak or starburst artifacts in the formation of such images. Such artifacts typically result from a sharp difference in signal attenuation at the boundary of the metal implants and a patient's anatomy.

That is, high density objects such as metal present in the body of patients can cause severe artifacts that hinder a diagnosis. These artifacts may be caused due to several factors such as beam-hardening, scatter, photon starvation, partial volume, aliasing, and under-range in the data acquisition, as examples. The artifacts can be reduced by known metal artifact reduction (MAR) techniques. For instance, advanced beam-hardening, noise reduction, and scatter correction have been proposed for standard filtered back-projection algorithm. In another example, an iterative reconstruction algorithm for MAR incorporates the shape of the metal and may use a polyenergetic model to reduce beam-hardening artifacts. These algorithms belong to a category generally referred to as model-based algorithms.

In addition to the category of model-based algorithms, another class of algorithms can be described as "sinogram in-painting". In this class of algorithms, the sinogram data that is corrupted by the high-density object is discarded and replaced by either data interpolated using neighboring projections or data estimated by solving a cost function using some iterative algorithms, or by a forward projection of a prior image. These methods can be single steps or can involve successive refinements via an iterative process.

The efficacy of a given MAR technique depends on the type and amount of metal, as well as the size of the patient. However, typically a MAR technique is implemented in CT systems by prompting a user, such as a scanning technician, to initiate a MAR correction by activating a switch prior to the reconstruction process. If the MAR correction is activated, then the algorithm is implemented using a technique that is independent of the type of metal. That is, typically a MAR algorithm is a user option that may be selected, or not, during reconstruction. As such, titanium implants in hips or extremities are examples of low Z materials that may be treated in the same fashion as high Z material implants such as dental fillings or stainless steel.

Thus, there is a need to improve implementation of MAR algorithms in CT scanners.

Further, known methods for MAR correction can include model-based algorithms or sinogram in-painting. In sinogram in-painting, sinogram data that is corrupted by the high-density object is discarded and may be replaced by data interpolated using neighboring projections or data estimated by solving a cost function using some iterative algorithms, or by a forward projection of a prior image.

Pure interpolation techniques, however, may create additional artifacts in the reconstructed image due to inconsistency in the data. Hence two-pass techniques are more favorable in terms of artifact reduction. The first step is correction using an interpolation technique and the resultant first pass image is then used to generate a prior image. During the second pass the corrupted data is replaced by the forward projection of the prior image to generate the in-painted sinogram.

In a typical CT acquisition a prior image is not available and hence may be generated using corrupted data. In an ideal sense, the prior image should include any knowledge of the object without the high-density artifacts. Availability of an atlas, and then registering the images to the atlas, can in principle lead to a prior image. In practice, the prior image is typically generated by performing a non-linear transformation on either the original image or a first pass MAR image. However, it is often challenging to use the original image in the presence of metal (or high density) artifacts, and a first-pass MAR image typically has degraded information content close to the metal, thus the first-pass MAR image is not consistent with the original image, and non-linear processing will not add content to the prior image.

In another approach, the in-painted sinogram data can be combined with the original data to generate projection data which can then be fed to a reconstruction algorithm. This approach is general enough and can be used in conjunction with in-painted data generated using any of the methods described above. However, known in-painting techniques generally do not take into account the severity of the metal or high-density artifact.

Therefore, it would be desirable to improve image reconstruction when high-density objects are present.

BRIEF DESCRIPTION

Embodiments are directed toward a method and apparatus of reducing artifacts due to high-density objects in medical imaging.

According to one aspect, an imaging system includes a rotatable gantry for receiving an object to be scanned, a generator configured to energize an x-ray source to generate x-rays, a detector positioned to receive the x-rays that pass through the object, and a computer. The computer is programmed to obtain knowledge of a metal within the object, scan the object using system scanning parameters, reconstruct an image of the object using a reconstruction algorithm, and automatically select at least one of the system scanning parameters and the reconstruction algorithm based on the obtained knowledge.

According to another aspect, a method of imaging includes obtaining knowledge of a metal content within an object, automatically selecting at least one of system scanning parameters and a reconstruction algorithm based on the obtained knowledge, and reconstructing an image of the object.

According to yet another aspect, a computer readable storage medium having stored thereon a computer program comprising instructions, which, when executed by a computer, cause the computer to obtain knowledge of a metallic material that is positioned within an object, automatically select at least one of system scanning parameters and a reconstruction algorithm based on the knowledge of the metallic material, scan the object, and reconstruct an image of the object.

Various other features and advantages will be made apparent from the following detailed description and the drawings.

DETAILED DESCRIPTION

The operating environment of disclosed embodiments is described with respect to a sixty-four-slice computed tomography (CT) system. However, it will be appreciated by those skilled in the art that disclosed embodiments are equally applicable for use with other multi-slice configurations, or other imaging systems in general, such as an x-ray system on a c-arm or a micro-CT system, as examples. Moreover, disclosed embodiments will be described with respect to the detection and conversion of x-rays. However, one skilled in the art will further appreciate that embodiments are equally applicable for the detection and conversion of other high frequency electromagnetic energy. Disclosed embodiments will be described with respect to a "third generation" CT scanner, but is equally applicable with other CT systems as well as vascular and surgical C-arm systems and other x-ray tomography systems.

Figure 1:
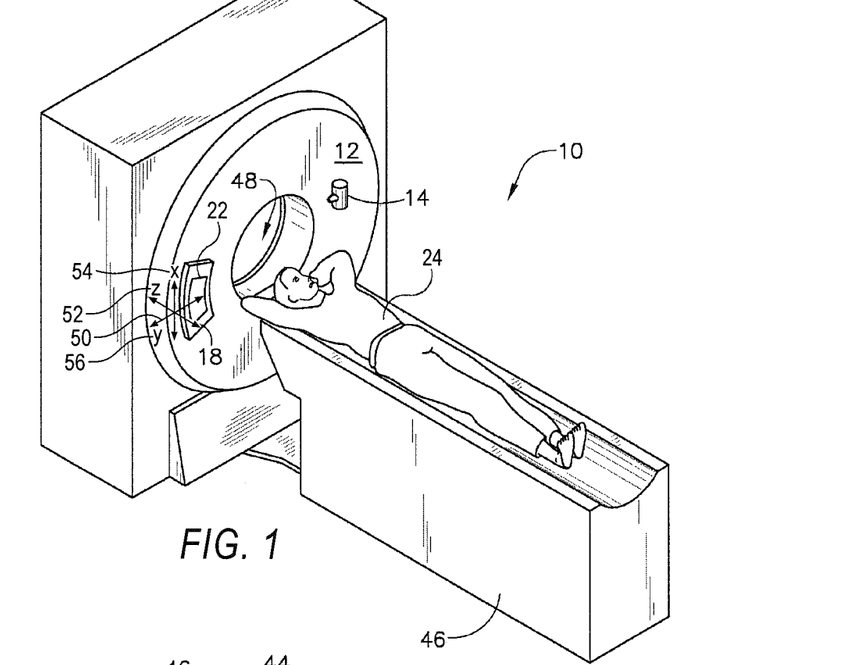
FIG. 1 is a pictorial view of a CT imaging system.
Figure 2:
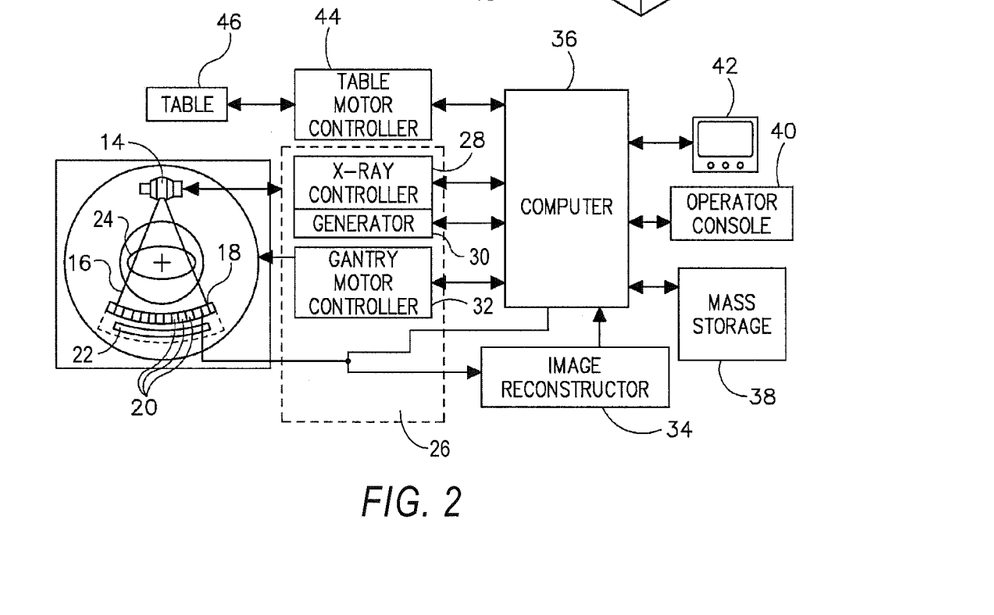
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. X-ray source 14 includes either a stationary target or a rotating target. Detector assembly 18 is formed by a plurality of detectors 20 and data acquisition systems (DAS) 22. The plurality of detectors 20 sense the projected x-rays that pass through a medical patient 24, and DAS 22 converts the data to digital signals for subsequent processing. Each detector 20 produces an analog electrical signal that represents the intensity of an impinging x-ray beam and hence the attenuated beam as it passes through patient 24. During a scan to acquire x-ray projection data, gantry 12 and the components mounted thereon rotate about a center of rotation 26.

Rotation of gantry 12 and the operation of x-ray source 14 are governed by a control mechanism 26 of CT system 10. Control mechanism 26 includes an x-ray controller 28 and generator 30 that provides power and timing signals to x-ray source 14 and a gantry motor controller 32 that controls the rotational speed and position of gantry 12. An image reconstructor 34 receives sampled and digitized x-ray data from DAS 22 and performs high speed image reconstruction. The reconstructed image is applied as an input to a computer 36 which stores the image in a mass storage device 38.

Computer 36 also receives commands and scanning parameters from an operator via an operator console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 22, x-ray controller 28, and gantry motor controller 30. In addition, computer 36 operates a table motor controller 44 which controls a motorized table 46 to position patient 24 and gantry 12. Particularly, table 46 moves patients 22 through a gantry opening 48 in whole or in part. A coordinate system 50 for detector assembly 18 defines a patient or Z-axis 52 along which patient 24 is moved in and out of opening 48, a gantry circumferential or X-axis 54 along which detector assembly 18 passes, and a Y-axis 56 that passes along a direction from a focal spot of X-ray tube 14 to detector assembly 18.

X-ray source 14, in accordance with present embodiments, is configured to emit x-ray beam 16 at one or more energies. For example, x-ray source 16 may be configured to switch between relatively low energy polychromatic emission spectra (e.g., at approximately 80 kVp) and relatively high energy polychromatic emission spectra (e.g., at approximately 140 kVp). As will be appreciated, x-ray source 14 may also be operated so as to emit x-rays at more than two different energies. Similarly, x-ray source 14 may emit at polychromatic spectra localized around energy levels (i.e., kVp ranges) other than those listed herein (e.g., 100 kVP, 120 kVP, etc.). Selection of the respective energy levels for emission may be based, at least in part, on the anatomy being imaged.

In some embodiments X-ray controller 28 may be configured to selectively activate x-ray source 14 such that tubes or emitters at different locations within system 10 may be operated in synchrony with one another or independent of one another. In certain embodiments discussed herein, the x-ray controller 28 may be configured to provide fast-kVp switching of x-ray source 14 so as to rapidly switch source 14 to emit X-rays at the respective polychromatic energy spectra in succession during an image acquisition session. For example, in a dual-energy imaging context, x-ray controller 28 may operate x-ray source 14 so that x-ray source 14 alternately emits x-rays at the two polychromatic energy spectra of interest, such that adjacent projections are acquired at different energies (i.e., a first projection is acquired at high energy, the second projection is acquired at low energy, the third projection is acquired at high energy, and so forth). In one such implementation, fast-kVp switching operation performed by x-ray controller 28 yields temporally registered projection data. In some embodiments, other modes of data acquisition and processing may be utilized. For example, a low pitch helical mode, rotate-rotate axial mode, N×M mode (e.g., N low-kVp views and M high-kVP views) may be utilized to acquire dual-energy datasets.

Techniques to obtain energy sensitive measurements include: (1) scan with two distinctive energy spectra and (2) detect photon energy according to energy deposition in the detector. Such measurements provide energy discrimination and material characterization, and may be used to generate reconstructed images using a base material decomposition (BMD) algorithm. A conventional BMD algorithm is based on the concept that, in an energy region for medical CT, the x-ray attenuation of any given material can be represented by a proper density mix of two materials with distinct x-ray attenuation properties, referred to as the base or basis materials. The BMD algorithm computes two CT images that represent the equivalent density of one of the base materials based on the measured projections at high and low x-ray photon energy spectra, respectively.

Thus, CT image data is obtained that may be from a single or a dual energy application. CT reconstruction is generally a two-step process. The patient is placed on the scanner and an x-ray beam is caused to rotate about the patient, either in a helical or an axial operation. Detectors measure the pattern of radiation (projection) transmitted through the patient. Image reconstruction from the projections is performed using a filtered backprojection (FBP). Metal artifacts arise because the attenuation coefficient for diagnostic x-rays in metal is much higher than in soft tissue or bone. Thus, the CT projection of the object may contain a region, in the shadow of the metal object, where virtually no radiation is detected. Reconstructions using FBP leads to artifacts from the inconsistency in the projection data.

Figure 3:
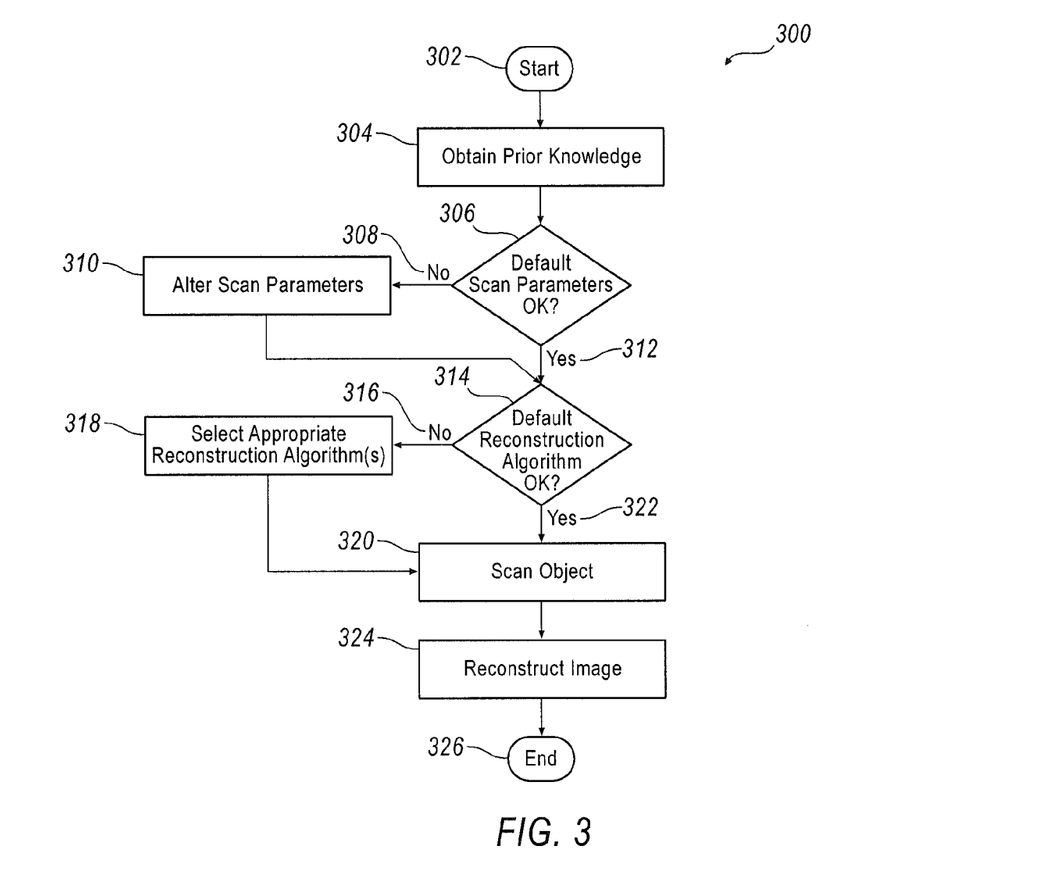
FIG. 3 is an example of an automatic metal artifact reduction technique or algorithm.

Referring now to FIG. 3, a metal artifact reduction technique or algorithm 300 is set forth according to one example. Algorithm 300 may be implemented using a computer, such as computer 36 as illustrated in FIG. 2. Starting at step 302, prior knowledge of metal content within a patient is obtained at step 304. The prior knowledge may be obtained using a scout scan, wherein the scout scan includes one of a 2D scan, a tomosynthesis scan, a 3D scan, and a dual energy scan, as examples. The prior knowledge of the may also be obtained in patient files or by interviewing the patient, and thus may be based on a known patient history such that a type of implant is known prior to scanning the object. The prior knowledge obtained may include the metal content, such as a type of metal, and the type of metal may include titanium, gold, or stainless steel, as examples.

Once the prior knowledge is obtained, system scanning parameters and/or a reconstruction algorithm are selected based on the obtained knowledge. That is, once the scout scan is performed or the prior knowledge is otherwise obtained and uploaded, system scan parameters and a metal-specific reconstruction may be automatically and intelligently selected that are not based on typical or default scanning default parameters. Typically, default scanning parameters are used based on the type of scan being performed, such as in a single energy or a dual energy scan. A default gantry tilt angle is also used that may be 0° as well. However, depending on the type of metal, or combination of metals, and their location, scanning parameters may be altered to account for such information. Thus, at step 306, scanning parameters are assessed based on the prior knowledge obtained at step 304. If the default parameters are not acceptable 308, then scan parameters are automatically altered at step 310 (that is, without human intervention). The scan parameters altered may include but are not limited to monoenergetic scanning kV, a monoenergetic scanning mA, dual/multi energy scanning (kV and mA), and the gantry tilt angle. For example, if the scout scan indicates that the scanned object is not exceedingly large and the metal objects are not exceedingly attenuating, of if the prior knowledge of the implant (i.e., patient history) indicates this as well.

In addition, based on the prior knowledge of the metal implant obtained at step 304, the reconstruction algorithm may be automatically selected as well to account for the type of metal in the implant.

A default reconstruction may be implemented having a default MAR algorithm as well. Typically, a default acquisition and reconstruction may include acquiring or accessing an initial projection dataset or initial view dataset and performing a standard reconstruction of the initial projection dataset to generate an initial reconstructed CT image dataset. A metal mask is generated by first applying a threshold to the reconstructed image dataset and subsequently optionally applying morphological operations to modify the mask. The metal mask is used to indicate locations of metal voxels within the image dataset. The metal mask is forward projected onto the projection data to identify detector pixels containing metal, or dexels, in the initial view dataset. Detectors cells marked as being impacted by the metal mask are completed via a weighted three-dimensional interpolation. An optional smoothing is applied to the interpolated patch before replacing the metal dexels in the initial view dataset with the completed patch. The completed projection data is reconstructed to generate a final CT image dataset. Because former metal voxels may be improperly represented in the final CT image dataset, the metal voxels are replaced in the final CT image dataset with modified and smoothed image voxels corresponding to the metal voxel locations. In a multi-energy context, the projection interpolation, interpolation patch smoothing, and metal replacement may be applied in a joint fashion to preserve the physical meaning of the BMD images. However, this correction technique is independent of the type of metal. But, because the nature of the metal drives the nature of the artifacts, the default correction algorithm is not particularly directed toward all types of metal implants that may be encountered.

According to another method, a first image may be obtained at a first energy spectrum, and a second image may be obtained at a second energy spectrum using a dual energy scan. A metal artifact correction signal is extracted using the first image and the second image, or using a first reconstructed image and a second reconstructed image that are generated respectively from the first and second images. The metal artifact correction on the first reconstructed image is performed using the metal artifact correction signal to generate a first corrected image.

That is, a projection-space correction approach is used to compensate for the metal artifacts. The approach utilizes images or a set of images at two different energy spectrums derived from original dual energy scans. The severity of artifacts from a scanned metal object within the reconstructed images changes with different X-ray tube voltages. However, the appearance or signature of the artifacts within the reconstructed images is similar regardless of the X-ray spectrum. The projection-space correction approach takes advantage of the similar or common artifact signatures to extract a metal artifact correction signal for correcting the original reconstructed images via image processing manipulations, while minimizing the impact on residual signals from normal anatomies such as the soft tissue and bones. For example, the projection-space correction approach may be used for highly attenuating metals (e.g., stainless steel) that generate artifacts. In addition, the projection-space correction approach takes into account the difference in Hounsfield units (HU) of the images across different X-ray tube voltages, the selection of data to be used for generating the artifact signature, and motion. This method may work very well for low Z implants but additional processing may be included in the case of high Z implants in which case photon starvation occurs.

In fact, known MAR methods, in general, are independent of the type of metal, and can be categorized into two main groups. Sinogram completion methods assume that the projection measurements through a metal are missing or incorrect. Accordingly, these projections are disregarded and image reconstruction is performed using limited data. However, sinogram completion methods sometimes indicate a tradeoff in different aspects of image quality. Metal artifacts may be reduced, but new artifacts may be introduced in the process and there may also be a loss of spatial resolution.

The second group includes methods that attempt to reduce the mismatch between the monochromatic reconstruction model of FBP and the beam hardening effects that occur. In such techniques, all information in the projections is retained and therefore the reduction of the artifacts depends on the accuracy of the model and the physical limitations of the detectors. However, beam hardening correction methods may only be effective when sufficient photons pass through the implant and requires prior knowledge of the implant material or x-ray spectrum.

According to some known methods, metal artifacts may be reduced when combining for missing projections and beam hardening. For instance, one known method preserves information in projection measurements through lower-attenuating implants that do not fully attenuate the x-ray beam and only replace those projections through higher-attenuating implants that are unavailable because of complete attenuation. This method first determines locations and types of implants in the patient, implements a physics correction by reducing beam hardening errors in projections through lower-attenuating implants, and iteratively replaces missing projections through higher-attenuating implants before image reconstruction. However, this process as well requires prior knowledge of the implant material.

Thus, according to the disclosed embodiment and referring still to FIG. 3, after automatically altering the scan parameters at step 310 or if the default scan parameters suffice 312, at step 314 method 300 assesses whether the default reconstruction algorithm is sufficient based on the prior knowledge of the metal content obtained at step 304. If not 316, then a reconstruction algorithm appropriate to and specific to the metal identified at step 304 is selected at step 318 and scanning proceeds at step 320. Alternatively, if the default reconstruction algorithm is the appropriate algorithm 322, then scanning proceeds 320 and an image is reconstructed at step 324. Method 300 ends at step 326.

As such, in general an intelligent and automatic acquisition and reconstruction includes obtaining prior knowledge of a patient implant via a scout scan or via access to patient history records, as examples. The type of implant and location are identified and system scanning parameters and/or MAR reconstruction algorithm are automatically selected or altered, based on the prior information obtained (i.e., type or location of metal) and without human intervention.

That is, an intelligent workflow is disclosed where a scout scan that precedes the actual scan is used to determine the location and type of a high-density object such as metal. The high-density object is automatically detected, and the reconstruction engine is triggered to perform the artifact correction. Upon automatic detection of the high-density object, a special metal (or high-density) specific acquisition is performed for the views impacted by the metallic or high-density object.

Also, a user controlled workflow is disclosed wherein the correction algorithm is specific to the nature of the metal. Artifacts from low density implants such as titanium are primarily introduced from spectral artifacts and can be reduced using a beam hardening correction algorithm, as an example. A combination of algorithms can be used for high-density implants such as stainless steel or dental fillings. The combined algorithms can include beam hardening followed by sinogram in-planting, as an example. A user can be given an option to choose the correction algorithm based on the type of metal. In one example, the user feeds the type of metal to the reconstruction engine, and the reconstruction engine decides automatically the type of correction based on the user input.

As discussed, various MAR algorithms include "sinogram in-painting". In this class of algorithms and as stated, the sinogram data that is corrupted by the high-density object is discarded and replaced by either data interpolated using neighboring projections or data estimated by optimizing a cost function using iterative algorithms, or by a forward projection of a prior image. Pure interpolation techniques may create additional artifacts in the reconstructed image due to inconsistency in the data. Hence techniques based on forward projection of a prior image may be more robust in terms of artifact reduction, creating less additional artifacts.

Figure 4:
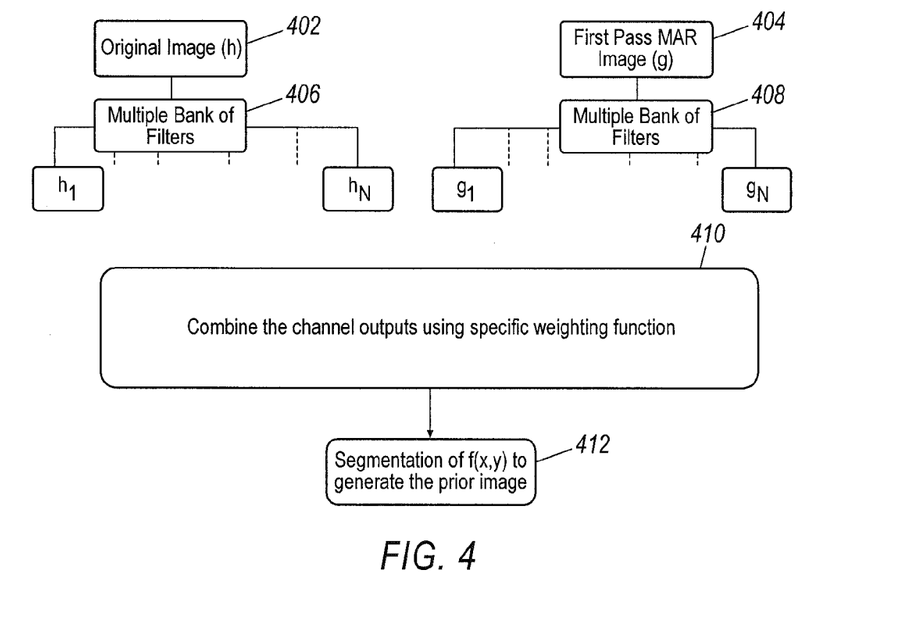
FIG. 4 is an example of a multi-band filtering artifact reduction technique.

In a typical CT acquisition a prior image is not available and hence may be generated using corrupted data. In ideal sense, the prior image should include any knowledge of object without the high-density artifacts. Availability of an atlas and then registering the images to the atlas can in principle lead to a prior image. In practice, the prior image is typically generated by performing a non-linear transformation on either the original image or a first pass MAR image. Thus, referring to FIG. 4, disclosed herein is an advanced signal processing method of algorithm 400 in which the prior image is generated using both original image 402 and the first-pass MAR image 404. The two images can be first passed through a respective bank of filters, 406 and 408. The filter output from the original image can be combined 410 with that of the first pass MAR image using weights specific for each channel according to the following equation:

$$f(x,y) = \Sigma \alpha_i(x,y) h_i(x,y) + \Sigma \beta_i(x,y) g_i(x,y); \quad \text{Eqn. 1.}$$

Thus, anatomic details of the original image are preserved in the proximity of the metal without re-introducing the high-density artifacts, and the prior image is generated 412.

A prior image introduces constraints during the replacement step. That is, constraints in the sinogram domain during the replacement step can be considered as prior information. The prior image in this context is the image of the object without the metallic (or high-density) implants. However in a typical CT acquisition such prior image is not available and hence is generated using corrupted data (i.e., with metal artifacts).

Thus, according to method 400, information from both the original and first-pass MAR image is used to generate the prior image. As such, method 400 includes a signal processing algorithm for generating the prior image to reduce high-density artifacts. Specifically anatomic detail is retained without loss of resolution, and these features are retained in FBP reconstruction of the original sinogram. However, the anatomic detail are somewhat blurred in first-pass MAR reconstruction in the vicinity of the metal. Simultaneously, it is desired to remove the metal artifacts (high frequency as well as low frequency streaks), and these artifacts appear in the original FBP reconstruction, but are significantly reduced in first-pass MAR image. Method 400 combines the best information from original FBP and first pass MAR images, described mathematically in the following multi-band filtering equation and as shown in FIG. 4, wherein h(x,y), g(x,y) are the original and first pass MAR image, respectively, and $h_l(x,y)$, l=1...N and $g_l(x,y)$, l=1...N denote the output from the multi-band filtering of the original and the first pass MAR image. Each filter output is combined using specially designed weights, $\alpha_l(x,y)$, $\beta_l(x,y)$ that are spatially varying. The weights will vary as a function of the distance from the metal. One example of this would be the two channel method where N=2. One example of the weighting function can be $\alpha_1=0$, $\alpha_2=m(x,y)$ and correspondingly $\beta_1=1$, $\beta_2=1-m(x,y)$ where m(x,y) is a weighting function which is a function of distance from the metallic object.

The prior image, in one example, is generated using multi-band filtering in Fourier space. Alternatively these images can be combined in any transformed domain such as wavelet. As another example, the prior image can be generated by registering the first pass MAR image to an atlas of metal absent images that can be obtained from the patient history.

Thus, multi-band filtering combines in purely image space in which resultant reconstructed images are generated using prior images generated with multi-band filtering followed by segmentation.

As stated, it can be challenging to generate uncorrupted or in-painted data to replace corrupted portions of the sinogram. Thus, in an alternative to multi-band filtering, the in-painted sinogram can be generated by performing a smart combination of the original projection and corrected projection generated by the in-painting process. That is, projection data can be adaptively combined as follows.

The disclosed high-density artifact correction algorithm of FIG. 4 can include multiple algorithms and a part of the correction algorithm replaces data corrupted from the metallic (or high density) object using in-painted data that is consistent and uncorrupted from the metallic object. The in-painted data is generated using a forward projection of the prior image, and the prior image is an image of the object without the metallic (or high-density) implants. The prior image can be generated from an atlas (or library) of images without implants. That is, a number of images without implants may be accessed to generate the prior image, as one example. The prior image is generated using multi-band filtering of the original FBP and the first-pass MAR image.

Figure 5:
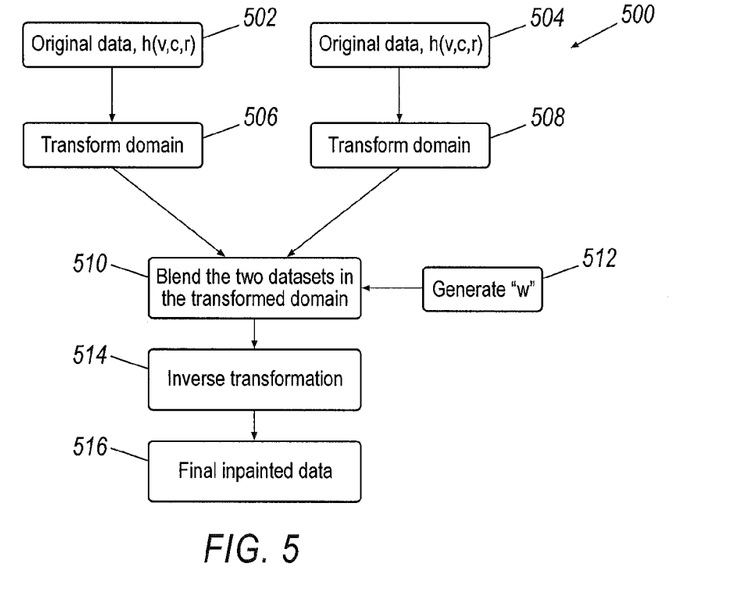
FIG. 5 is an example of adaptive combination of projection data.

Method 400 of FIG. 4 is purely image-based. Alternatively, and referring to FIG. 5, the in-painted sinogram can be generated by performing a smart combination 500 of the original projection and corrected projection generated by the in-painting process. An advantage of this non-linear processing is to obtain corrected images that are consistent with the uncorrected images. Original data h(v,c,r) is obtained at step 502 and in-painted data g(v,c,r) at step 504. Domain transform occurs 506, 508 to the desired or needed domain, such as a wavelet transform. The two datasets are combined at step 510, per the following equation:

$$p(v, c, r) = \sum_{k,l} w_{k,l}(v, c, r) h^k(v, c, r) g^l(v, c, r);. \qquad \text{Eqn. 2}$$

The process of combining the two datasets is adaptive and depends on the severity of the metal artifact. A weighting factor, w is data-dependent and is a fidelity measure for the sinogram data. The factor w can be computed 512 using direct approaches such as the estimated signal-to-noise ratio for the detector sample or it can be computed using indirect approaches such as a forward projection of the metallic object. An inverse transform is performed 514 that corresponds to the transform conducted at steps 506, 508, and the final in-painted data is generated at step 516. The proposed adaptive combination of the two datasets of FIG. 5 can be combined with algorithm 400 of FIG. 4. Alternatively, it can also be used standalone in case a second-pass approach is not used to generate the in-painted data.

Further, metal-corrected images may be generated using adaptive combination of the original projection data and the in-painted data. The in-painted data can be generated using iterative techniques that are either based on reducing an objective function, forward projection of the prior image, or using interpolation techniques. The weighting, w is adaptive and is a function of the attenuation of the rays from the metallic (or high-density) object. The process of combining the two datasets can be performed in the original radon domain or any transformed domain such as wavelet, multi-band filter etc.

Figure 6:
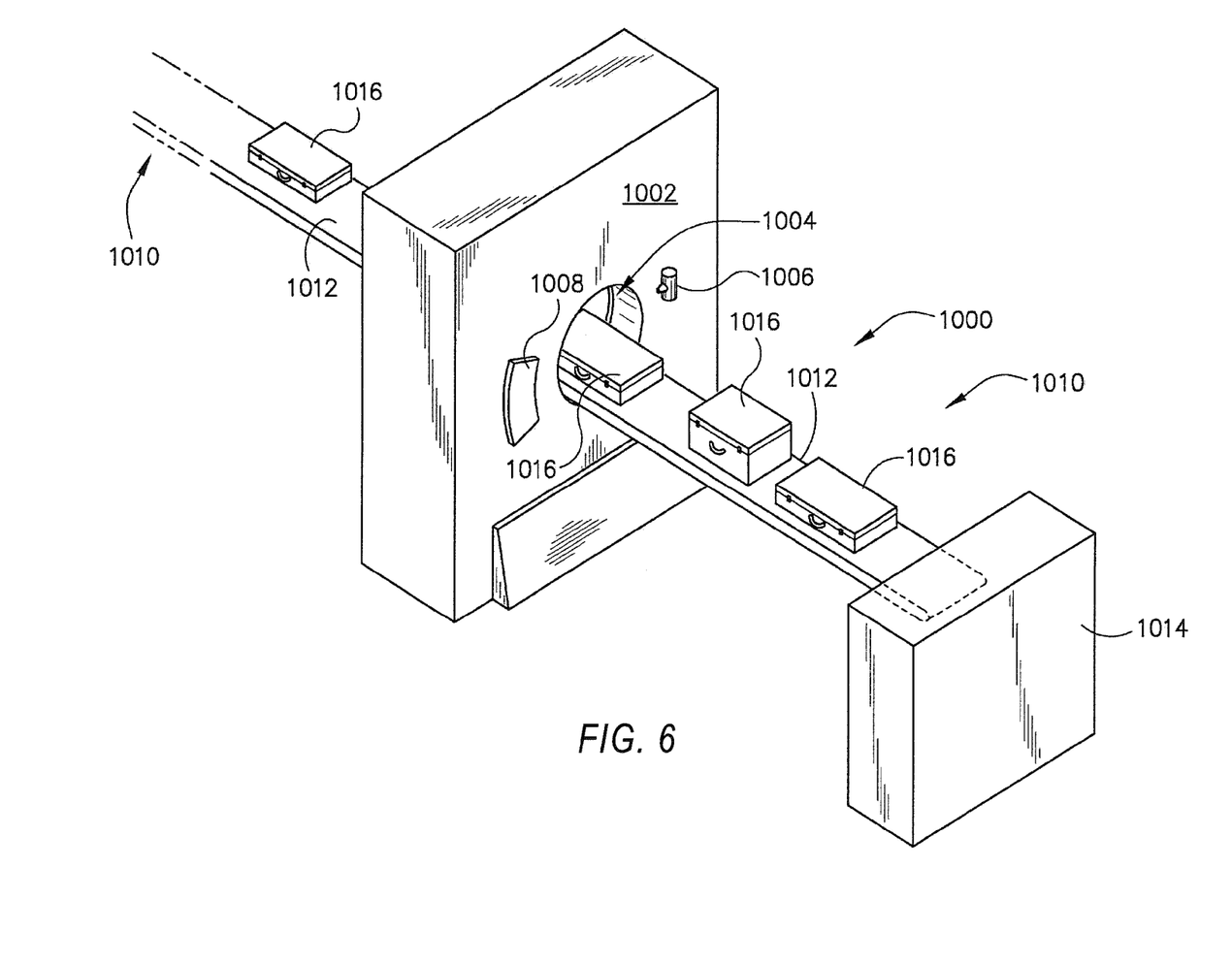
FIG. 6 is a pictorial view of a CT system for use with a non-invasive package inspection system.

Referring now to FIG. 6, there is shown a package/baggage inspection system 1000 that can use the image acquisition and reconstructions techniques according to embodiments disclosed and which includes a rotatable gantry 1002 having an opening 1004 therein through which packages or pieces of baggage may pass. The rotatable gantry 1002 houses one or more x-ray energy sources 1006 as well as a detector assembly 1008 having scintillator arrays comprised of scintillator cells. A conveyor system 1010 is also provided and includes a conveyor belt 1012 supported by structure 1014 to automatically and continuously pass packages or baggage pieces 1016 through opening 1004 to be scanned. Objects 1016 are passed through opening 1004 by conveyor belt 1012, imaging data is then acquired, and the conveyor belt 1012 removes the packages 1016 from opening 1004 in a controlled and continuous manner. As a result, postal inspectors, baggage handlers, and other security personnel may non-invasively inspect the contents of packages 1016 for explosives, knives, guns, contraband, etc.

An implementation of system 10 and/or 1000 in an example comprises a plurality of components such as one or more of electronic components, hardware components, and/or computer software components. A number of such components can be combined or divided in an implementation of the system 10 and/or 1000. An exemplary component of an implementation of the system 10 and/or 1000 employs and/or comprises a set and/or series of computer instructions written in or implemented with any of a number of programming languages, as will be appreciated by those skilled in the art. An implementation of system 10 and/or 1000 in an example comprises any (e.g., horizontal, oblique, or vertical) orientation, with the description and figures herein illustrating an exemplary orientation of an implementation of the system 10 and/or 1000, for explanatory purposes.

An implementation of system 10 and/or system 1000 in an example employs one or more computer readable signal bearing media. A computer-readable signal-bearing medium in an example stores software, firmware and/or assembly language for performing one or more portions of one or more implementations. An example of a computer-readable signal-bearing medium for an implementation of the system 10 and/or the system 1000 comprises the recordable data storage medium of the image reconstructor 34, and/or mass storage device 38 of computer 36. A computer-readable signal-bearing medium for an implementation of the system 10 and/or the system 1000 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 1000, for instance, one or more of a telephone network, a local area network ("LAN"), a wide area network ("WAN"), the Internet, and/or a wireless network.

According to one embodiment, an imaging system includes a rotatable gantry for receiving an object to be scanned, a generator configured to energize an x-ray source to generate x-rays, a detector positioned to receive the x-rays that pass through the object, and a computer. The computer is programmed to obtain knowledge of a metal within the object, scan the object using system scanning parameters, reconstruct an image of the object using a reconstruction algorithm, and automatically select at least one of the system scanning parameters and the reconstruction algorithm based on the obtained knowledge.

According to another embodiment, a method of imaging includes obtaining knowledge of a metal content within an object, automatically selecting at least one of system scanning parameters and a reconstruction algorithm based on the obtained knowledge, and reconstructing an image of the object.

According to yet another embodiment, a computer readable storage medium having stored thereon a computer program comprising instructions, which, when executed by a computer, cause the computer to obtain knowledge of a metallic material that is positioned within an object, automatically select at least one of system scanning parameters and a reconstruction algorithm based on the knowledge of the metallic material, scan the object, and reconstruct an image of the object.

A technical contribution for the disclosed method and apparatus is that it provides for a computer-implemented apparatus and method of reducing artifacts due to high-density objects in medical imaging.

When introducing elements of various embodiments of the disclosed materials, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

While the disclosed materials have been described in detail in connection with only a limited number of embodiments, it should be readily understood that the embodiments are not limited to such disclosed embodiments. Rather, that disclosed can be modified to incorporate any number of variations, alterations, substitutions or equivalent arrangements not heretofore described, but which are commensurate with the spirit and scope of the disclosed materials. Furthermore, while single energy and dual-energy techniques are discussed above, that disclosed encompasses approaches with more than two energies. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. An imaging system comprising:
    a rotatable gantry with a bore for receiving an object to be scanned;
    an x-ray source attached to the gantry;
    a generator attached to the gantry configured to energize the x-ray source to generate x-rays;
    a detector attached to the gantry, positioned to receive the x-rays; and
    a computer programmed to:
        obtain knowledge of metal within the object, wherein the knowledge obtained of the metal includes a type of metal and a position of the metal;
        instruct the system to perform a scan of the object, using system scanning parameters based on the obtained knowledge, to generate scan data;
        reconstruct an image of the object from scan data using a reconstruction algorithm automatically selected based on the type of metal.

2. The imaging system of claim 1, wherein the computer is further programmed to automatically select the at least one of the system scanning parameters and the reconstruction algorithm without human intervention.

3. The imaging system of claim 1, wherein the computer is further programmed to obtain the knowledge using a computed tomography (CT) scout scan, wherein the scout scan includes at least one of a 2D scan, a tomosynthesis scan, a 3D scan, and a dual energy scan.

4. The imaging system of claim 1, wherein the computer is further programmed to process an image specific to the position of the metal.

5. The imaging system of claim 1, wherein the knowledge of the metal type is based on a known patient history such that a type of implant is known prior to scanning the object.

6. The imaging system of claim 1, wherein the computer is programmed to automatically select the system scanning parameters that include at least one of a monoenergetic scanning kV, a monoenergetic scanning mA, dual energy scanning, and a gantry tilt angle and, when multiple type of metallic objects are present, data acquisition is specific to a location of the metal.

7. The imaging system of claim 1, wherein the reconstruction of the image further comprises:
    generating a metal mask by applying a threshold to an image dataset;
    forward projecting the metal mask to identify detector pixels containing metal;
    interpolating the detector pixels containing metal via a weighted three-dimensional interpolation; and
    applying smoothing to the interpolated detector pixels.

8. The imaging system of claim 1, wherein the reconstruction of the image further comprises replacing metal voxels with modified and smoothed image voxels corresponding to metal voxel locations.

9. A method of imaging comprising:
obtaining knowledge of a metal content within an object, wherein the knowledge obtained of the metal includes a type of metal and a position of the metal within the object;
automatically selecting at least one of system scanning parameters and a reconstruction algorithm based on the obtained knowledge;
instructing a medical imaging system to perform a scan of the object, using at least one of the system scanning parameters, to generate scan data; and
reconstructing an image of the object from scan data using a reconstruction algorithm automatically selected based on the type of metal.

10. The method of claim 9, wherein automatically selecting further comprises automatically selecting using a computing device and without human intervention.

11. The method of claim 9, wherein obtaining knowledge of the metal content further comprises obtaining a computed tomography (CT) scout scan of the object, the scout scan comprising one or more of a 2D scan, a tomosynthesis scan, a 3D scan, and a dual energy scan.

12. The method of claim 9, wherein obtaining the knowledge of the metal content comprises accessing a known patient history such that a type of implant is known prior to scanning the object.

13. The method of claim 9, wherein automatically selecting comprises automatically selecting the system scanning parameters that include at least one of a monoenergetic scanning kV, a monoenergetic scanning mA, dual energy scanning, and a gantry tilt angle, and when multiple types of metallic objects are present, data acquisition is specific to the location of each metal type.

14. The method of claim 9, wherein the reconstruction of the image further comprises:
generating a metal mask by applying a threshold to an image dataset;
forward projecting the metal mask to identify detector pixels containing metal;
interpolating the detector pixels containing metal via a weighted three-dimensional interpolation; and
applying smoothing to the interpolated detector pixels.

15. The method of claim 9, wherein the reconstruction of the image further comprises replacing metal voxels with modified and smoothed image voxels corresponding to metal voxel locations.

* * * * *